(12) United States Patent
Song

(10) Patent No.: US 10,709,765 B2
(45) Date of Patent: Jul. 14, 2020

(54) COMPOSITION FOR INHIBITING SURVIVAL OR GROWTH OF TUBERCLE BACILLUS BY ADJUSTING POLARIZATION OF MACROPHAGE, AND METHOD USING SAME

(71) Applicant: THE INDUSTRY & ACADEMIC COOPERATION IN CHUNGNAM NATIONAL UNIVERSITY (IAC), Daejeon (KR)

(72) Inventor: Chang-Hwa Song, Daejeon (KR)

(73) Assignee: THE INDUSTRY & ACADEMIC COOPERATION IN CHUNGNAM NATIONAL UNIVERSITY (IAC), Daejeon (KR)

(*) Notice: Subject to any disclaimer, the term of this patent is extended or adjusted under 35 U.S.C. 154(b) by 0 days.

(21) Appl. No.: 16/315,607

(22) PCT Filed: Jul. 4, 2017

(86) PCT No.: PCT/KR2017/007061
§ 371 (c)(1),
(2) Date: Jan. 4, 2019

(87) PCT Pub. No.: WO2018/008932
PCT Pub. Date: Jan. 11, 2018

(65) Prior Publication Data
US 2019/0307850 A1    Oct. 10, 2019

(30) Foreign Application Priority Data
Jul. 5, 2016    (KR) .................. 10-2016-0084770

(51) Int. Cl.
| A61K 39/04 | (2006.01) |
| A61K 39/00 | (2006.01) |
| A61K 38/21 | (2006.01) |
| A61P 31/06 | (2006.01) |
| A61K 31/133 | (2006.01) |
| A61K 31/4409 | (2006.01) |
| A61K 31/496 | (2006.01) |
| A61K 31/4965 | (2006.01) |
| A61K 31/739 | (2006.01) |
| A61K 35/15 | (2015.01) |
| A61K 45/06 | (2006.01) |

(52) U.S. Cl.
CPC .......... *A61K 38/217* (2013.01); *A61K 31/133* (2013.01); *A61K 31/4409* (2013.01); *A61K 31/496* (2013.01); *A61K 31/4965* (2013.01); *A61K 31/739* (2013.01); *A61K 35/15* (2013.01); *A61K 38/21* (2013.01); *A61K 39/00* (2013.01); *A61K 45/06* (2013.01); *A61P 31/06* (2018.01)

(58) Field of Classification Search
CPC ......... A61K 39/00; A61K 39/02; A61K 39/04
USPC ............................ 424/9.1, 9.2, 234.1, 248.1
See application file for complete search history.

(56) References Cited

U.S. PATENT DOCUMENTS

| 8,895,536 B2 | 11/2014 | Bannister et al. |
| 2006/0257359 A1 | 11/2006 | Francois et al. |
| 2015/0147300 A1* | 5/2015 | Woodell-May ...... C12N 5/0645 424/93.7 |

FOREIGN PATENT DOCUMENTS

| KR | 100972304 B1 | 7/2010 |
| KR | 1020130091061 A | 8/2013 |

OTHER PUBLICATIONS

Huang, Z., et al., PLOS ONE, vol. 10, pp. 1-16, Jun. 2015.*
International Search Report for PCT/KR2017/007061 dated Aug. 30, 2017.
Jae Seuk Park et al., "The Effect of IFN-y on the Phagocytosis of *Mycobacterium tuberculosis* and Activation of Human Pulmonary Alveolar Macrophage", Tuberculosis and Respiratory Diseases, Feb. 1998, pp. 36-44, vol. 45, No. 1.
Simeone Marino et al., "Macrophage Polarization Drives Granuloma Outcome during *Mycobacterium tuberculosis* Infection", Infection and Immunity, Jan. 2015, pp. 324-338, vol. 83, No. 1.
Zikun Huang et al., "*Mycobacterium tuberculosis*-Induced Polarization of Human Macrophage Orchestrates the Formation and Development of Tuberculous Granulomas In Vitro", PLOS ONE, Jun. 19, 2015, pp. 1-16.

* cited by examiner

*Primary Examiner* — Rodney P Swartz

(57) ABSTRACT

The present invention provides a composition for inhibiting the survival or growth of a tubercle bacillus, containing a material which induces the polarization of a macrophage into an M1 macrophage, and a method for inhibiting the survival or growth of the tubercle bacillus by using the composition.

3 Claims, 5 Drawing Sheets

COMPOSITION FOR INHIBITING SURVIVAL OR GROWTH OF TUBERCLE BACILLUS BY ADJUSTING POLARIZATION OF MACROPHAGE, AND METHOD USING SAME

CROSS-REFERENCE TO RELATED APPLICATIONS

This application is a U.S. National Stage of International Patent Application No. PCT/KR2017/007061 filed Jul. 4, 2017, which claims the priority benefit of Korean Patent Application No. 10-2016-0084770, filed on Jul. 5, 2016, in the Korean Intellectual Property Office, the disclosures of which are incorporated herein by reference.

TECHNICAL FIELD

The present invention relates to a method for inhibiting the survival or proliferation of *Mycobacterium tuberculosis*, and a method for adjusting the polarization of macrophages therefor.

BACKGROUND ART

Tuberculosis is a chronic infectious disease caused by infection with *Mycobacterium tuberculosis* or other *Mycobacterium* species. Tuberculosis is one of major diseases in developing countries, as well as an increasing problem in developed countries, with about 8 million new patients and 3 million deaths each year. The infection may be asymptomatic for a considerable period of time. However, tuberculosis is most commonly manifested as an acute inflammation of the lungs, resulting in fever and non-productive cough. Moreover, if not treated, serious complications and death are typically caused.

Tuberculosis can be treated using antibiotic therapy over a long period of time, but such treatment is not sufficient to prevent the spread of tuberculosis. Infected individuals may be asymptomatic, but contagious, for a certain period of time. In addition, patient behavior is difficult to monitor although the treatment regimen is strictly followed. Some patients fail to complete the course of treatment, which may result in ineffective treatment and the development of drug resistance. Even after completion of the whole course of treatment, infection with *Mycobacterium tuberculosis* cannot be rooted out from infected individuals but still remains a latent infection that can be reactivated.

In order to control the spread of tuberculosis, effective vaccination and accurate early diagnosis of the disease are most important. Currently, vaccination with live bacteria is the most efficient way for inducing protective immunity. The most common *Mycobacterium* used for this purpose is Bacillus Calmette-Guerin (BCG), an avirulent strain of *M. bovis*. However, the stability and efficacy of BCG is an issue of controversy, and some countries, such as the US, do not vaccinate the general public with this agent. Thus, studies continue on a technique for preventing tuberculosis infection that is excellent in stability and efficacy, compared with previous techniques.

Diagnosis of tuberculosis is typically achieved using a skin test, which involves intradermal exposure to tuberculin purified protein derivative (PPD). Antigen-specific T cell responses result in measurable induration at the injection site by 48-72 hours after injection, which indicates exposure to *Mycobacterium* antigens. However, a problem of sensitivity and specificity arises with regard to this test, and individuals vaccinated with BCG cannot be distinguished from infected individuals.

Macrophages play an important role not only in natural immunity or inflammatory responses but also in acquired immune responses, and the representative function is presenting antigens to T cells (antigen presentation). Macrophages receive protein antigens by phagocytosis, decompose them into small peptides (antigen processing), and bind the decomposed peptides to their MHCs, to promote the activation of T cells again on the cell surface. Also, macrophages act as the principal effector cells that indicate immunological action in cell-mediated immune responses and humoral immune responses, as well as having the function of suggesting antigens required to initiate immune responses. Macrophages activated by T cells perform the function of removing antigens from a delayed-type hypersensitivity reaction, and macrophages have the function of removing antigens bound by antibodies, with phagocytosis.

The inventors of the present invention confirmed that *Mycobacterium tuberculosis* disturbs the M1 polarization of macrophages by secreting pathogenic factors and confirmed therefrom the inhibitory efficacy of survival or proliferation of *Mycobacterium tuberculosis* by inducing polarization of macrophages, thereby completing the present invention.

DETAILED DESCRIPTION OF INVENTION

Technical Task

The present invention is to provide a composition for inhibiting the survival or proliferation of *Mycobacterium tuberculosis* which has different mechanism from previous drugs and causes relatively fewer side effects, by using a material inducing the polarization of macrophages, and a method for inhibiting the survival or proliferation of *Mycobacterium tuberculosis* using the same.

Means for Solving the Task

An embodiment according to the present invention provides a composition for inhibiting the survival or proliferation of *Mycobacterium tuberculosis*, comprising a material inducing the polarization of macrophages into M1 macrophages.

The material inducing polarization may comprise at least one selected from the group consisting of lipopolysaccharide, interferon-gamma and inflammatory cytokines, for example, IL-6 and TNF-α.

The composition may comprise 1-20 ng/ml of lipopolysaccharide and 1-20 ng/ml of interferon-gamma.

Also, the composition may further comprise at least one anti-tuberculosis drug selected from the group consisting of rifampicin, isoniazid, ethambutol, pyrazinamide, streptomycin or analogues thereof.

The tuberculosis may be eye tuberculosis, skin tuberculosis, adrenal tuberculosis, renal tuberculosis, epididymal tuberculosis, lymph node tuberculosis, laryngeal tuberculosis, middle ear tuberculosis, intestinal tuberculosis, multi-drug-resistant tuberculosis, pulmonary tuberculosis, sputum tuberculosis, bone tuberculosis, throat tuberculosis, lymphatic gland tuberculosis, lung deficiency, breast tuberculosis or spinal tuberculosis.

Another embodiment according to the present invention provides a method for inhibiting the survival or proliferation of *Mycobacterium tuberculosis*, comprising inducing the polarization of macrophages into M1 macrophages using the composition.

The survival or proliferation of *Mycobacterium tuberculosis* may be inhibited by inducing the polarization of macrophages into M1 macrophages by the composition, and thereafter inducing apoptosis of the macrophages upon infection with *Mycobacterium tuberculosis*.

Advantageous Effect

The present invention shows the effect of inhibiting *Mycobacterium tuberculosis* by induction of macrophage polarization that was not previously known. According to the present invention, it is expected that not only typical *Mycobacterium tuberculosis* but also multidrug-resistant *Mycobacterium tuberculosis* to existing drugs can be prevented and treated.

BEST MODE FOR CARRYING OUT THE INVENTION

Figure 1A:
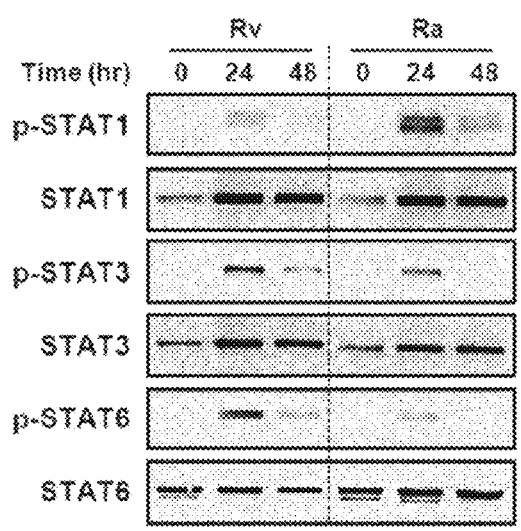
FIGS. 1A to 1D are electrophoresis photographs of protein expression using western blotting, which shows the expression of macrophage M1/M2 polarization markers upon infection with *Mycobacterium tuberculosis* in macrophages.

Interferon-gamma allows to have more enhanced antigen presenting ability than macrophages before encountering antigens, and also to increase complement-mediated phagocytosis and produce inflammatory cytokines. Such macrophages are so-called classically activated macrophages (M1).

Helper T lymphocytes can be divided into two major types, Th1 and Th2 cells, based on secreted cytokines. Cytokines which are mainly secreted by Th2 cells, such as IL-4, set macrophages in the state opposite to the activation induced by interferon-gamma, for example, increasing the expression of major histocompatibility antigen class. Macrophages in such state are called alternatively activated macrophages (M2).

In order to achieve the aforementioned objective, one embodiment according to the present invention provides a composition for inhibiting the survival or proliferation of *Mycobacterium tuberculosis*, comprising a material inducing the polarization of macrophages into M1 macrophages.

The material inducing polarization may comprise at least one selected from the group consisting of lipopolysaccharide, interferon-gamma and inflammatory cytokines, for example, IL-6 and TNF-α.

Specifically, the composition may comprise 1-20 ng/ml of lipopolysaccharide and 1-20 ng/ml of interferon-gamma.

Also, the composition may further comprise at least one anti-tuberculosis drug selected from the group consisting of rifampicin, isoniazid, ethambutol, pyrazinamide or analogues thereof.

The tuberculosis may be eye tuberculosis, skin tuberculosis, adrenal tuberculosis, renal tuberculosis, epididymal tuberculosis, lymph node tuberculosis, laryngeal tuberculosis, middle ear tuberculosis, intestinal tuberculosis, multidrug-resistant tuberculosis, pulmonary tuberculosis, sputum tuberculosis, bone tuberculosis, throat tuberculosis, lymphatic gland tuberculosis, lung deficiency, breast tuberculosis or spinal tuberculosis.

Another embodiment according to the present invention provides a method for inhibiting the survival or proliferation of *Mycobacterium tuberculosis*, comprising inducing the polarization of macrophages into M1 macrophages using the composition.

The method may further comprise steps before and after infection with *Mycobacterium tuberculosis*.

The survival or proliferation of *Mycobacterium tuberculosis* may be inhibited by inducing the polarization of macrophages into M1 macrophages by the composition, and thereafter inducing apoptosis of the macrophages upon infection with *Mycobacterium tuberculosis*.

Hereinafter, preferred embodiments of the method for inhibiting the survival and proliferation of intracellular *Mycobacterium tuberculosis* using the polarization of macrophages according to the present invention will be described in detail with reference to the accompanying drawings. The present invention is not limited to the embodiments described below but may be implemented into various embodiments. The present embodiments are provided simply to complete the disclosure of the present invention and help a person skilled in the art completely understand the scope of the present invention.

MODES FOR CARRYING OUT THE INVENTION

Example 1

In Vitro Experiment for Assessing Inhibitory Effect of Polarization of Macrophage on Survival of *Mycobacterium tuberculosis*

1. Step of Confirming which Roles the Polarization of Macrophage Plays Upon Infection with *Mycobacterium tuberculosis*

In order to analyze which roles the polarization of macrophages play upon infection with *Mycobacterium tuberculosis*, macrophage polarization induced by infection with *Mycobacterium tuberculosis* was confirmed. That is, the expression level of polarization markers was confirmed over time, after infection with pathogenic *Mycobacterium tuberculosis* (*Mycobacterium tuberculosis* H37Rv) and non-pathogenic *Mycobacterium tuberculosis* (*M tuberculosis* H37Ra) in the rate of 1 bacterium per cell, using bone marrow-derived macrophages (BMDMs), mouse-derived macrophages.

FIG. 1A is the result of confirmation on protein expression level of phospho-STAT1 (p-STAT1), a marker indicating M1 macrophage polarization, and phospho-STAT3 (p-STAT3) and phospho-STAT6 (p-STATE), markers indicating M2 macrophage polarization, in macrophages infected with *Mycobacterium tuberculosis*, using a western blotting method. It demonstrates that the expression of phospho-STAT3 and phospho-STAT6 which indicate M2 macrophage polarization increases over cultivation time in macrophages infected with pathogenic *Mycobacterium tuberculosis*. In contrast, it could be confirmed that the expression of phospho-STAT1 which indicates M1 macrophage polarization increases in macrophages infected with non-pathogenic *Mycobacterium tuberculosis*. (In the drawings, STAT1, STAT3 and STATE are internal controls; the rest is the same as above.)

Figure 1B:
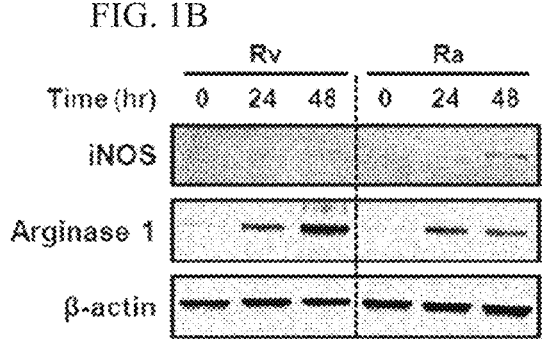
Figure 1C:
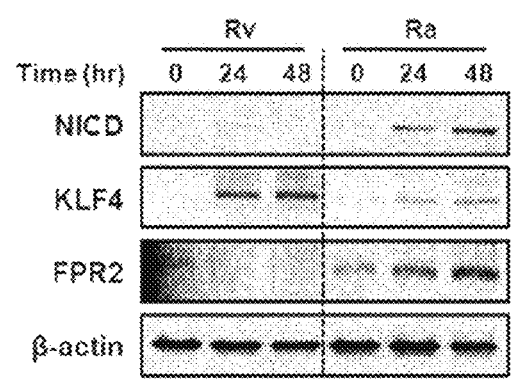
Figure 1D:
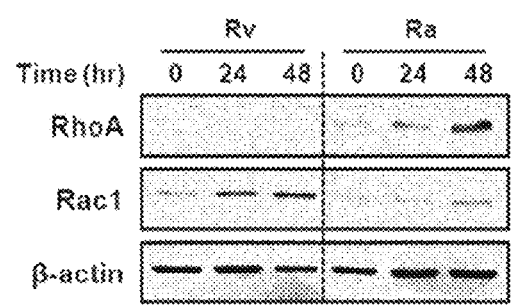

FIGS. 1B, 1C and 1D are the result of confirmation on protein expression level of iNOS, NICD, FPR2 and RhoA which indicate M1 macrophage polarization, and Arginase 1, KLF4 and Rac1 which indicate M2 macrophage polarization, in macrophages infected with H37Rv or H37Ra, using a western blotting method. It demonstrates that the expression of Arginase 1, KLF4 and Rac1 which indicate M2 macrophage polarization increases over cultivation time in macrophages infected with pathogenic *Mycobacterium tuberculosis*. In contrast, it could be confirmed that the expression of iNOS, NICD, FPR2 and RhoA which indicate M1 macrophage polarization increases in macrophages infected with non-pathogenic *Mycobacterium tuberculosis*. (In the drawings, β-actin is an internal control; the rest is the same as above.)

Also, Rv and Ra shown in FIG. 1 denote macrophages which are infected with H37Rv (pathogenic *Mycobacterium tuberculosis*) or H37Ra (non-pathogenic *Mycobacterium tuberculosis*) in the experiment. It means that the polarization of macrophages varies depending on the pathogenicity of *Mycobacterium tuberculosis*.

2. Step of Polarizing Mouse-Derived Macrophages into M1/M2

Mouse-derived macrophages were stimulated for 24 hours with lipopolysaccharide (10 ng/ml) and interferon-gamma (IFNγ) (10 ng/ml) to prepare M1 macrophages, and were stimulated for 24 hours with IL-4 (10 ng/ml) and IL-13 (10 ng/ml) to prepare M2 macrophages.

3. Step of Confirming Induction of Apoptosis after Infecting the Macrophages with *Mycobacterium tuberculosis*

Figure 2A:
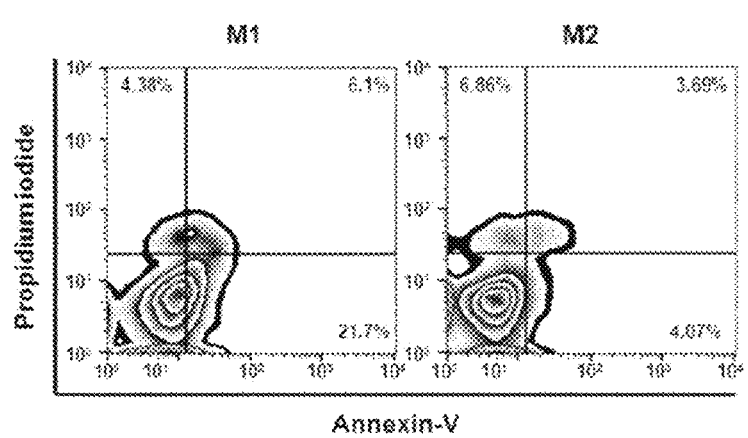
FIGS. 2A and 2B are drawings which show apoptosis induced by infection with *Mycobacterium tuberculosis* in M1/M2 macrophages.
Figure 2B:
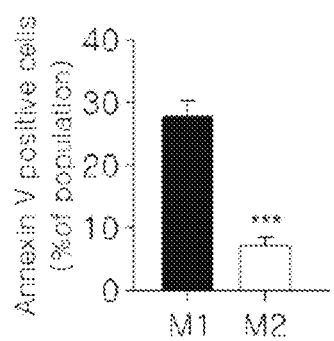
Figure 2C:
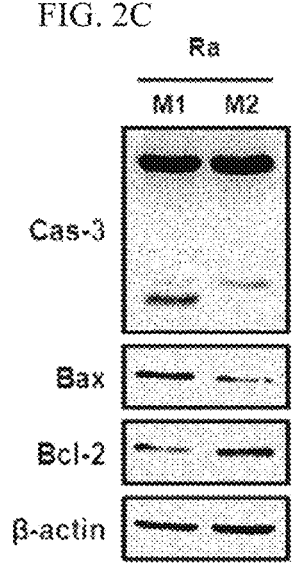
FIG. 2C is an electrophoresis photograph of protein expression using western blotting, which shows the activation of Caspase-3, Bax and Bcl-2 in M1/M2 macrophages infected with *Mycobacterium tuberculosis*.
Figure 2D:
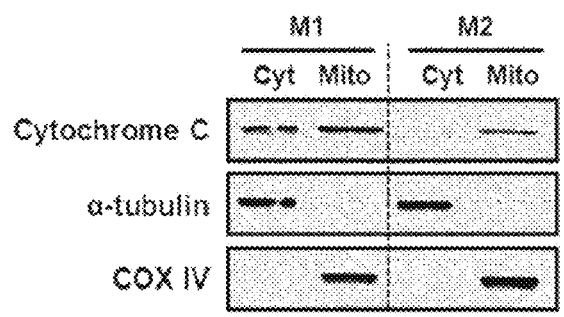
FIG. 2D is an electrophoresis photograph of protein expression using western blotting, which shows the intracellular transport of cytochrome C after isolating M1/M2 macrophages infected with *Mycobacterium tuberculosis* into cytoplasm and mitochondria.

FIG. 2A confirmed apoptosis using FACS after staining M1/M2 macrophages infected with *Mycobacterium tuberculosis* with Annexin-V/PI. FIG. 2B is a drawing which indicates the percentage of Annexin-V+/PI− cells by graph. It could be understood that upon infection with *Mycobacterium tuberculosis*, apoptosis is induced in M1 macrophages at a significantly higher rate than in M2 macrophages. FIG. 2C confirmed the induction of apoptosis in M1/M2 macrophages infected with *Mycobacterium tuberculosis*, using Caspase-3, Bax and Bcl-2. Similar to the result above, the expression of Caspase-3 and Bax increased, whereas the expression of Bcl-2 decreased, in M1 macrophages.

4. Step of Confirming Intracellular Transport of Cytochrome C after Infecting the Macrophages with *Mycobacterium tuberculosis*

Figure 3A:
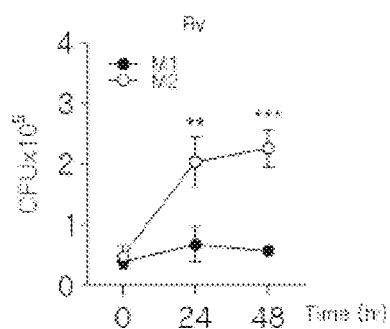
FIGS. 3A and 3B are graphs which measure the number of *Mycobacterium tuberculosis* intracellularly surviving in M1/M2 macrophages infected with *Mycobacterium tuberculosis*.
Figure 3B:
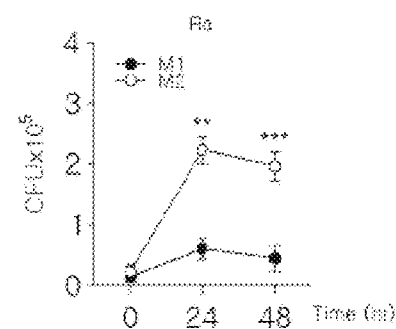
Figure 3C:
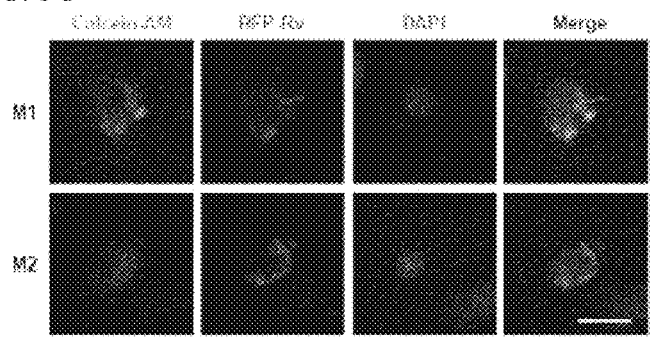
FIGS. 3C, 3D, 3E and 3F are drawings which show the intracellular survival of *Mycobacterium tuberculosis* in M1/M2 macrophages infected with *Mycobacterium tuberculosis*, through a fluorescence microscope.
Figure 3D:
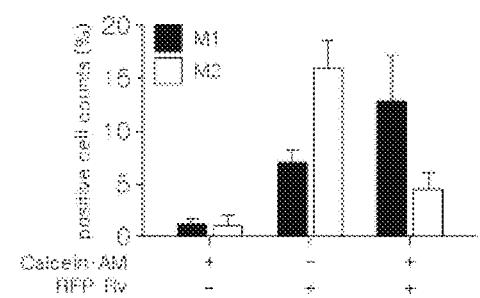

FIG. 3D is the result of confirmation on the intracellular transport of cytochrome C after isolating M1/M2 macrophages infected with *Mycobacterium tuberculosis* into cytoplasm and mitochondria. It was confirmed that upon infection with *Mycobacterium tuberculosis*, cytochrome C transport increases from mitochondria to cytoplasm in M1 macrophages. (In the drawings, α-tubulin is a cytoplasm control, and COX IV is a mitochondria control.)

According to the previous presentation of the present inventors, it was reported that apoptosis induced by *Mycobacterium tuberculosis* in macrophages is a significant mechanism for inhibition of intracellular survival of *Mycobacterium tuberculosis*. Therefore, it can be understood from the aforementioned experimental result that upon infection with *Mycobacterium tuberculosis*, M1 macrophages induce apoptosis and is thus more effective in inhibiting proliferation of *Mycobacterium tuberculosis*.

Example 2

Case of Using a Material Adjusting Macrophage Polarization and an Anti-Tuberculosis Drug in Combination 1. Experiment for Analyzing which Roles the Polarization of Macrophage Plays Upon Infection with *Mycobacterium tuberculosis*

In order to analyze which roles the polarization of macrophages play upon infection with *Mycobacterium tuberculosis*, the number of *Mycobacterium tuberculosis* within M1/M2 macrophages was measured.

Figure 3E:
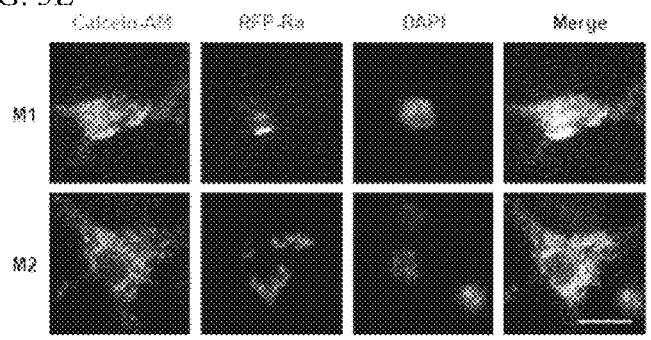
Figure 3F:
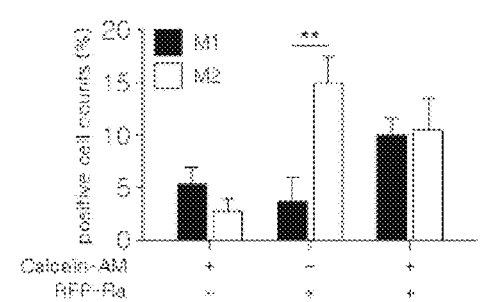

FIGS. 3A and 3B are graphs which show the result of cultivation for 24 and 48 hours under complete medium conditions, after washing extracellular *Mycobacterium tuberculosis* in M1/M2 macrophages which were infected with pathogenic *Mycobacterium tuberculosis* and non-pathogenic *Mycobacterium tuberculosis*, respectively, 3 hours after infection. In order to determine the number of intracellularly surviving *Mycobacterium tuberculosis*, cells were cultured in 7H10 agar medium for 14 to 21 days to calculate the total number of viable bacteria. FIGS. 3C and 3E are drawings which show *Mycobacterium tuberculosis* surviving in M1/M2 macrophages 48 hours after infection, using a fluorescence microscope, which are indicated by graph in FIGS. 3D and 3F. It could be confirmed that upon infection with *Mycobacterium tuberculosis*, *Mycobacterium tuberculosis* was controlled in M1 macrophages more effectively than in M2 macrophages.

Figure 4:
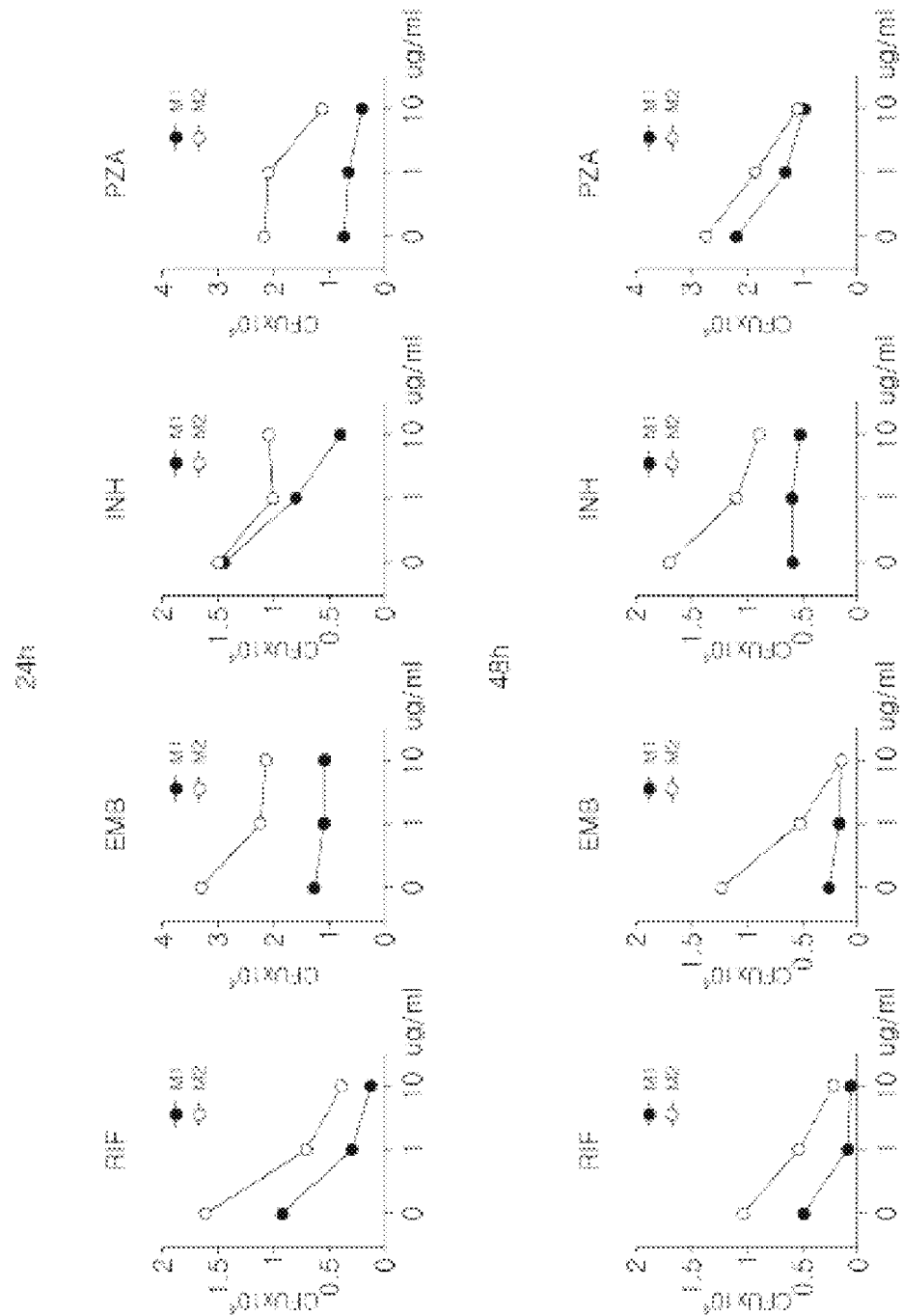
FIG. 4 is a graph which measures the number of intracellular *Mycobacterium tuberculosis* in M1/M2 macrophages infected with *Mycobacterium tuberculosis* upon the use of an anti-tuberculosis drug in combination.

2. Experiment for Confirming the Inhibitory Effect on the Survival of *Mycobacterium tuberculosis* by Using a Material Adjusting Macrophage Polarization and an Anti-Tuberculosis Drug in Combination FIG. 4 measured the number of intracellular *Mycobacterium tuberculosis* after washing extracellular *Mycobacterium tuberculosis* and treating an anti-tuberculosis drug (Rifampicin: RIF, Ethambutol: EMB, Isoniazid: INH, Pyrazinamide: PZA) or an anti-tuberculosis drug together with a material inducing M1/M2 macrophage polarization (LPS+IFNγ or IL-4+IL-13) in combination thereon, 3 hours after infecting macrophages with *Mycobacterium tubercu-* losis, and performing cultivation for 24 and 48 hours. As a result of experiment, it was confirmed that upon treatment of an anti-tuberculosis drug alone, the number of *Mycobacterium tuberculosis* was reduced, and particularly, the survival of *Mycobacterium tuberculosis* was inhibited more efficiently in cells induced into M1 polarization. By comparison, it was demonstrated that the survival of *Mycobacterium tuberculosis* was not effectively inhibited in M2 macrophages, in spite of treatment of an anti-tuberculosis drug.

Therefore, based on the aforementioned experimental result of M1 macrophages and the already known fact that an anti-tuberculosis drug inhibits the survival of *Mycobacterium tuberculosis*, it was determined that the adjustment of macrophage polarization together with the administration of an anti-tuberculosis drug would be more effective in killing *Mycobacterium tuberculosis*, and the hypothesis was verified.

Example 3

In Vivo Experiment for Assessing Inhibitory Effect of Polarization of Macrophage on Survival of *Mycobacterium tuberculosis* (Mouse Model)

1. Step of Polarizing Mouse-Derived Macrophages into M1/M2

Mouse-derived macrophages were stimulated for 24 hours with lipopolysaccharide (10 ng/ml) and interferon-gamma (IFNγ) (10 ng/ml) to prepare M1 macrophages, and were stimulated for 24 hours with IL-4 (10 ng/ml) and IL-13 (10 ng/ml) to prepare M2 macrophages.

2. Experiment for Assessing Inhibitory Effect of the Polarization of Macrophages on Survival of *Mycobacterium tuberculosis* after Infecting the Macrophages with *Mycobacterium tuberculosis*

Figure 5A:
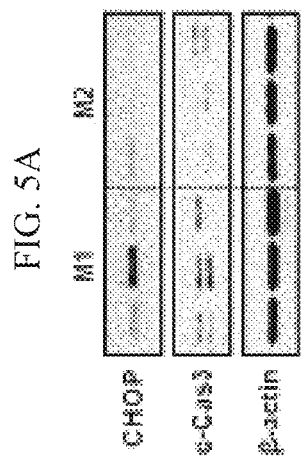
FIG. 5A is an electrophoresis photograph of protein expression using western blotting, which shows the activation of CHOP and Caspase-3 in lung tissues 20 days after infection with *Mycobacterium tuberculosis* through the nasal cavity in M1/M2 mouse models.
Figure 5B:
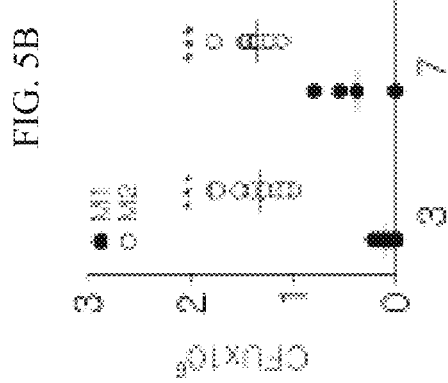
FIG. 5B is a graph which measures the number of *Mycobacterium tuberculosis* surviving in the lung tissues of M1/M2 mouse models infected with *Mycobacterium tuberculosis*.
Figure 5C:
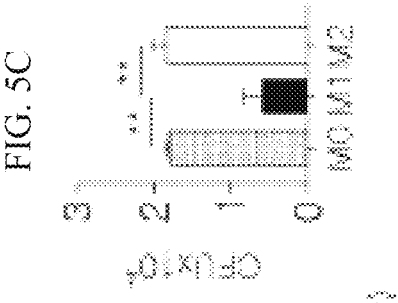
FIG. 5C is a graph which measures the number of *Mycobacterium tuberculosis* surviving in the lung tissues in M1/M2 mouse models infected with *Mycobacterium tuberculosis* upon the use of an anti-tuberculosis drug in combination.

FIG. 5A is the result of protein expression level of CHOP and Caspase-3 in the lung tissues of M1/M2 mouse models 20 days after infection by infecting M1/M2 mouse models with *Mycobacterium tuberculosis* through the nasal cavity, using a western blotting method. It could be observed that the activation of apoptosis is remarkably higher in the lung tissues of M1 mouse model than in those of M2 mouse model. FIG. 5B is a graph which shows the result of measuring the number of *Mycobacterium tuberculosis* surviving in the lung tissues of M1/M2 mouse models 3, 7 and 20 days after infection with *Mycobacterium tuberculosis*. FIG. 5B is a graph which shows the result of measuring the number of *Mycobacterium tuberculosis* surviving in the lung tissues of M1/M2 mouse models 3 days after infection with *Mycobacterium tuberculosis*, after infecting M1/M2 mouse models with *Mycobacterium tuberculosis*, and then administering 10 mg/kg of an anti-tuberculosis drug (a mixture of RIF, EMB, INH and PZA) through drinking water (1.5 ml/10 g mouse weight). It could be confirmed that the survival of *Mycobacterium tuberculosis* is more advantageous in the lung of M2 mouse model than in that of mouse model, even upon administration of the anti-tuberculosis drug. Similar to the result of in vitro experiment, in in vivo experiment, it appears that it would be more effective in inhibiting the proliferation of *Mycobacterium tuberculosis* by inducing apoptosis in M1 mouse model upon infection with *Mycobacterium tuberculosis*.

It was confirmed from the above experiment that the polarization of macrophages is adjusted according to the pathogenicity of *Mycobacterium tuberculosis*, and that upon infection with *Mycobacterium tuberculosis*, macrophages polarized into M1 have a remarkably high ability to inhibit the intracellular growth of *Mycobacterium tuberculosis* using apoptosis. By comparison, M2 macrophages provide an advantageous environment to the intracellular survival of *Mycobacterium tuberculosis*, and thus *Mycobacterium tuberculosis* having stronger pathogenicity induces the polarization into M2 macrophages. The present result proves that it is possible to control the intracellular survival of *Mycobacterium tuberculosis* by adjusting the polarization of macrophages.

What is claimed is:

1. A composition for inhibiting the survival or proliferation of *Mycobacterium tuberculosis*, the composition comprising:
   a material inducing the polarization of macrophages into M1 macrophages, and
   at least one anti-tuberculosis drug selected from the group consisting of rifampicin, isoniazid, ethambutol, pyrazinamide, and analogues thereof.

2. The composition of claim 1, wherein the material inducing polarization of macrophages into M1 macrophages comprises at least one selected from the group consisting of lipopolysaccharide, interferon-gamma, IL-6, and TNF-α.

3. The composition of claim 1, wherein the material inducing the polarization of macrophages into M1 macrophages includes 1-20 ng/ml of lipopolysaccharide and 1-20 ng/ml of interferon-gamma.

* * * * *